United States Patent [19]

Plucinski

[11] Patent Number: 4,944,730
[45] Date of Patent: Jul. 31, 1990

[54] ORGANIZER AND DISPENSER FOR BLOOD SAMPLE NEEDLE HOLDERS

[75] Inventor: Andrzej J. Plucinski, Norwood, N.J.
[73] Assignee: Becton, Dickinson and Company, Franklin Lakes, N.J.
[21] Appl. No.: 235,138
[22] Filed: Aug. 23, 1988
[51] Int. Cl.$^5$ .............................................. A61M 5/32
[52] U.S. Cl. ...................................... 604/187; 211/13
[58] Field of Search ..................... 211/74, 13, 60.1; 248/309.1, 312, 312.1, 316.8; 206/305, 363, 364, 443, 485; 604/187, 322

[56] References Cited

U.S. PATENT DOCUMENTS

| | | | |
|---|---|---|---|
| 2,954,876 | 12/1957 | Mathews | 211/74 |
| 4,367,738 | 1/1983 | Legendre et al. | 604/187 X |
| 4,479,800 | 10/1984 | Chester | 604/187 |
| 4,782,957 | 11/1988 | Kernodle, Sr. | 211/74 X |
| 4,867,746 | 9/1989 | Dufresne | 604/192 |

Primary Examiner—Richard J. Apley
Assistant Examiner—Rachel M. Healey
Attorney, Agent, or Firm—Robert P. Grindle

[57] ABSTRACT

An organizer and dispenser device is provided for holding and dispensing a plurality of blood sample needle holders maintained at a nursing station for use sequentially during the taking of blood samples from patients. The elongated device of the invention includes a rack-like body with opposed walls for maintaining the base flanges of the needle holders in orderly fashion and for dispensing the holders one by one. The basic u-shaped structure may include one or more modifications for holding the bases of the needle holders in place prior to dispensing. Also, the basic u-shaped structure may be duplicated back-to-back for doubling the quantity of holders available for dispensing.

7 Claims, 3 Drawing Sheets

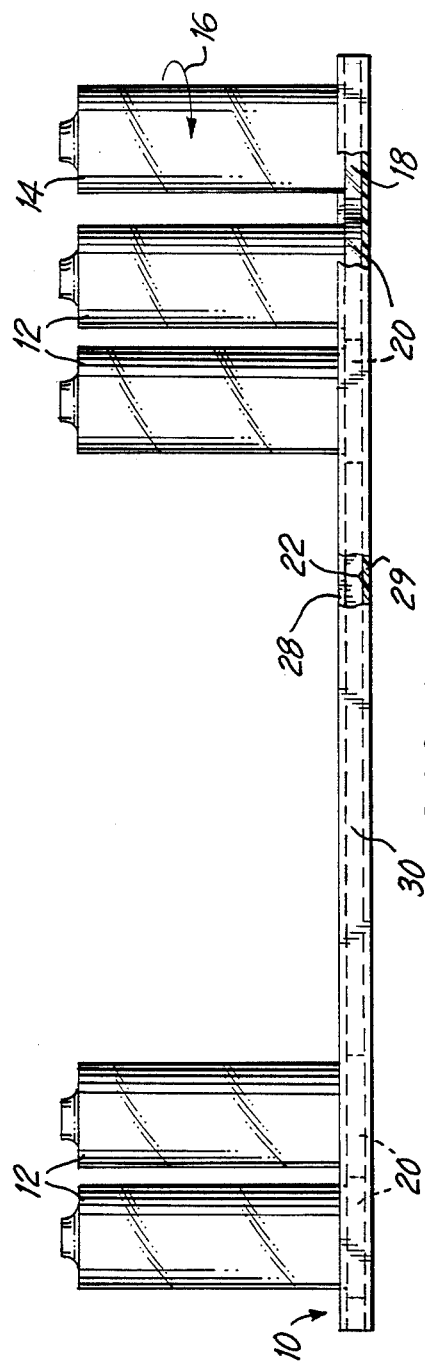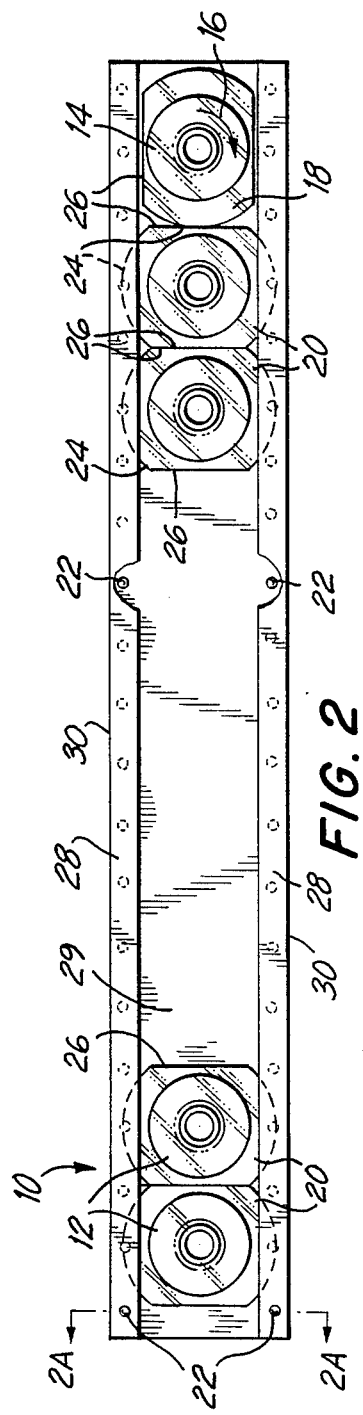

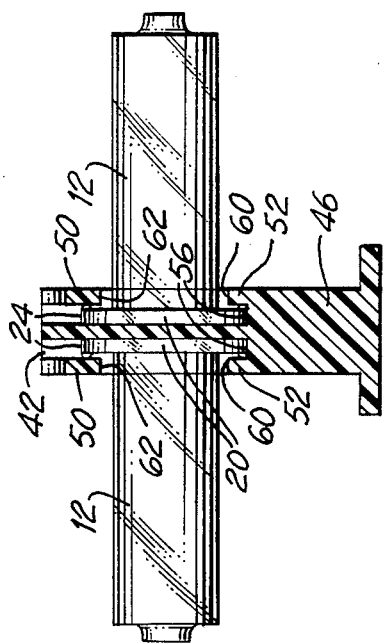
FIG. 3
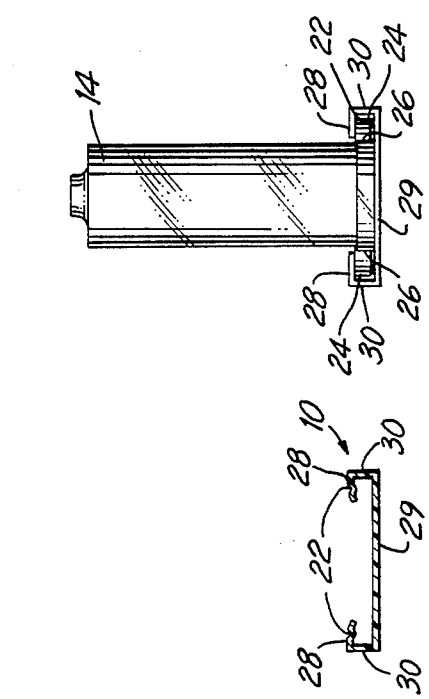
FIG. 5
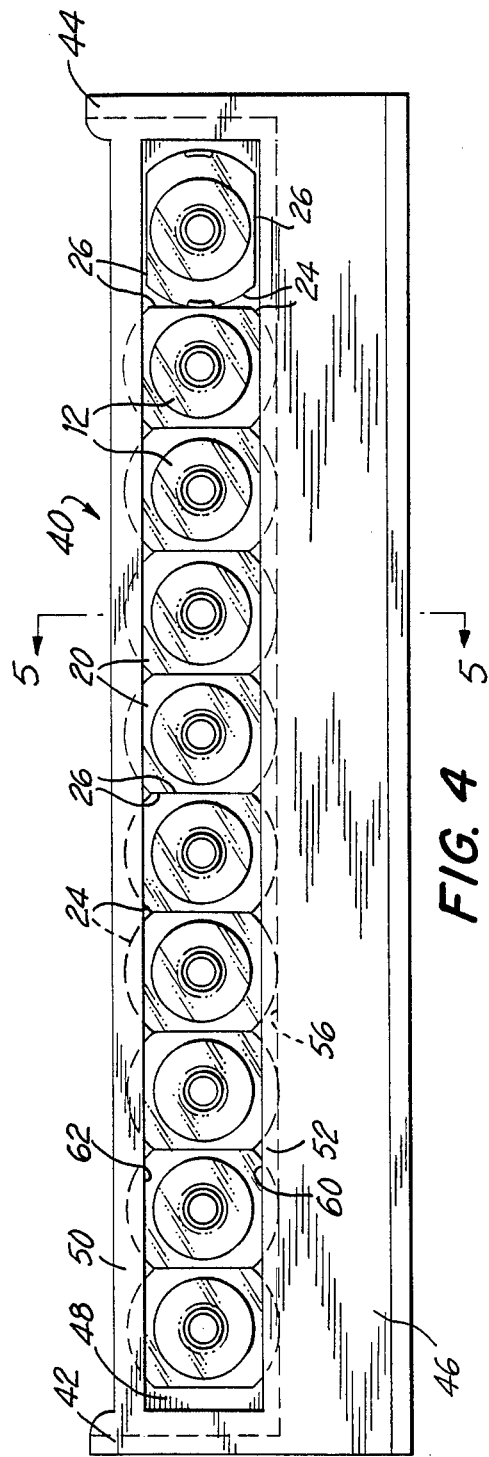
FIG. 2A
FIG. 4

ORGANIZER AND DISPENSER FOR BLOOD SAMPLE NEEDLE HOLDERS

BACKGROUND AND DESCRIPTION OF THE INVENTION

This invention relates generally to holders used for holding needles (as well as blood sample tubes) which are, in turn, utilized for taking blood samples. More particularly, this invention relates to a device which will retain, in orderly fashion, a plurality of such needle holders for sequential dispensing of the holders at a nursing station, for example, so that a nurse or laboratory technician may obtain from the organizer device of the invention a holder for holding an evacuated tube, for example, for taking a blood sample or a plurality of blood samples from an individual patient at a single blood sample taking procedure.

As practitioners in the art will understand, blood sample needle holders of the type to which the invention here is directed are used in large quantities in the everyday operations of a hospital, doctor's office, clinics or clinical laboratories. The holders are tube-shaped and have an open end and a substantially closed end. The substantially closed end has positioned centrally thereof screw threads for receiving the hub of a two ended needle. Once the needle is in place, the needle end extending away from the holder is utilized by the clinician for insertion into the vein of a patient. The opposite end of the double-ended needle extends into the holder. This needle end is inserted through the stopper of a blood collection tube when that tube is inserted into the needle holder. Once the needle is in place in the patient's vein, a plurality of evacuated tubes may be inserted into the open end of the holder for receiving the one end of the needle for taking, sequentially, a plurality of different samples of blood from a single patient at one blood taking.

Because the blood sample may be contaminated and because the holders are exposed to such contamination, once such a blood taking procedure takes place, the needle holder is discarded to avoid contamination, along with the associated needles which have been screwed into the substantially closed end of the holder. Because of this continuous disposal of the holders, a great quantity of such holders are utilized on a daily basis. For this reason, it has become important to have an organizer and dispensing device which will maintain the holders in orderly fashion in the phlebotomist's tray or cart so that they may be easily grasped from the device and utilized by the nurse or laboratory technician in the environment wherein a patient anticipates having a needle inserted into the skin. It is to this environment that the invention is directed.

The organizer device of the invention is an elongated rack-like structure with opposed L-shaped walls extending from an elongated base. The individual needle holders, therefore, can be inserted into the device of the invention by having the base flanges thereof slid between the opposed L-shaped walls for retaining the base flanges of the holders in place. The opposed L-shaped walls are spaced apart from each other so that the remainder of the holders extend upwardly from the base of the organizer and dispensing device of the invention.

Because of the unique configuration of the base flanges of the needle holders, they may be inserted through the opposed spaced apart upper surfaces of the u shaped structures of the organizer device of the invention. That is, the base flanges of the holders have diametrically opposed straight sides on two sides thereof and diametrically opposed curved sides on the remaining two sides thereof. As a consequence, the distance between the two diametrically opposed straight sides is substantially smaller than the distance between the remaining two curved sides. Because of this, the needle holders may be inserted into the organizer device of the invention and twisted 90° to remain held in place until it is desired to obtain one of the holders for use. Thereafter, the clinical or lab technician may simply twist a holder 90° and remove the base from the opposed upright locking surfaces of the organizer device of the invention.

Needle holders of the type to which this invention is directed are comprised of a flexible thermoplastic material, usually transparent or translucent in order to allow visual observation of blood flow inside the needle holders. Some holders have base flanges which are relatively thick and non-flexible. For these, the organizer of the invention may be comprised of a flexible material in order to provide a cooperating frictional grip between the needle holder flanges and the organizer of the invention. On the other hand, some needle holders have comparatively thin flexible base flanges, in which case the organizer may be less flexible to accommodate this property. The differences discussed here will be apparent from the discussion below.

As a further feature of the invention, the elongated base plate of the organizer device of the invention may be configured to provide a spring action for wedging the relatively non flexible base flanges of the needle holders in place so that they are gripped frictionally for maintaining them in place in an orderly fashion prior to dispensing. Alternatively, and/or additionally, the base structure may include a plurality of spaced apart nipples or protuberances which may extend integrally from the base plate of the organizer device of the invention for engaging the side edges of the base flanges of the holders for maintaining them in place. Alternatively, these protuberances or dimples may be formed subsequently by heat deflection. Also, as will be understood they may be formed to extend downwardly from the overhanging flanges of the organizer of the invention. At any rate, these protuberances may be comprised of a flexible thermoplastic material which "gives" when the base flange of a holder is forced over them for dispensing the holder.

Before describing this invention in more detail, it may be well to note that the dispenser organizer device of the invention may be comprised of a flexible thermoplastic material such as, for example, polystyrene, polypropylene, polyethylene, polyvinyl chloride, polycarbonate and polyethylene terephthalate. Also, they may be comprised of rolled metallic sheet material formed into the desired shape. The device of the invention may be comprised of a moldable part which can be mass produced, as will be understood, from one of the above-noted materials. Materials should be selected which will provide a degree of resiliency for the purposes of providing cooperative organization of the needle holders, as discussed above, and as discussed further in more detail below.

Other objects and advantages of this invention will be apparent from the following description, the accompanying drawings, and the appended claims.

Description of the Drawings

FIG. 1 is a side elevational view of one embodiment illustrating the invention particularly for use with needle holders having non flexible bases;

FIG. 2 is a top plan view of the device shown in FIG. 1, partially broken away;

FIG. 2A is a sectional view taken along lines 2A—2A of FIG. 2 in a somewhat modified form;

FIG. 3 is an end elevational view of the device shown in FIG. 1 as viewed from the right-hand end thereof;

FIG. 4 is a side elevational view of a further embodiment illustrating the invention in the form of a double clip holder organizer for storing double the number of needle holders as that shown in the embodiment of FIG. 1;

FIG. 5 is a sectional view taken along lines 5—5 of FIG. 4;

Detailed Description of the Invention

Figure 6:
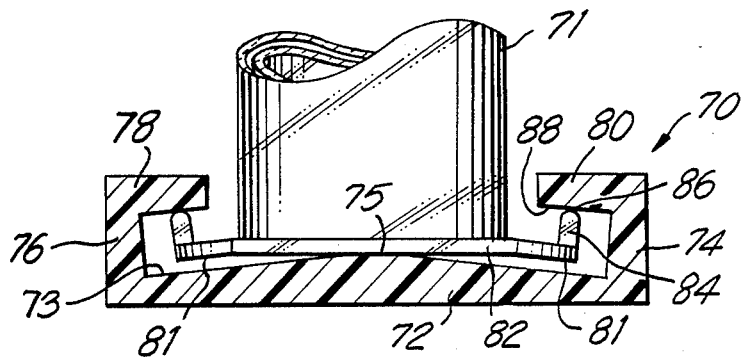
FIG. 6 is a sectional view of a further embodiment of the invention illustrating one form of retention arrangement for holding the individual needle holders with flexible base flanges in place in the dispenser organizer device of the invention.

Referring to the drawings in which like reference characters refer to like parts throughout the several views thereof, FIGS. 1, 2, 2A and 3 show one embodiment of the dispenser organizer device of the invention generally designated 10 in the form of an elongated base 29 having at each side thereof opposed upright walls 30 with horizontal integral extension flanges 28 extending cantilever therefrom in opposed relation to each other. As can be seen in FIGS. 1, 2 and 3, a plurality of needle holders 12 are positioned in the device 10. Each of the bases 20 of the needle holders 12 are inserted between the opposed walls and flanges 28, 30 of the device 10. As can best be seen in FIG. 2, each holder 12 has two diametrically opposed curved side edges 24 on their bases 20, and two diametrically opposed straight edges 26.

Referring now to FIG. 2, as can be seen, the one needle holder 14 at the extreme right hand end of the device 10 has been turned so its diametrically opposed surfaces 26 on its base 18 are positioned so that the holder base 18 may be removed up through the opening provided by the spaced apart flanges 28. This arrangement is also shown in the side elevational view in FIG. 3 wherein the straight side edges 26 of the base are positioned so that the holder 14 may be lifted out of the organizer holder device 10. As can be seen further in FIG. 2, the remaining holders 12 positioned in the organizer device 10 are all turned 90° from the position of the holder 14. Thus, the rounded edges 24 of their bases 20 are positioned underneath the opposed horizontal surfaces of flanges 28 which maintains the holders 12, as shown in the figures, in place until such time as they are rotated 90° for removal.

Referring further to FIG. 2, a plurality of protuberances 22 are shown positioned in spaced apart relation along the floor 29 surface. These protuberances serve to extend upwardly between the individual bases 20 of the holders 12 for engaging and maintaining them positioned along the device 10. Alternatively, as discussed above, protuberances 22 may extend downwardly from the bottom surfaces of flanges 28 as shown in FIG. 2A. Moreover, as shown in FIG. 2A they may be formed by heat deflection.

In this connection, it will be understood that these protuberances are comprised of a thermoplastic material which "gives" when bases 20 of holders 12 are moved along the device 10 so that they may be forced, if required into appropriate positions in spaced apart fashion along the holder device 10. However, as discussed above, each individual needle holder 12 may be rotated 90° for relatively simple removal of the individual holders sequentially as they are required for use.

In addition, as a further feature of the invention, device 10 may be comprised of a flexible material to accommodate needle holders with relatively non-flexible base flanges. In this case, the opposed cantilever flanges are formed as shown in FIG. 2A to have a downwardly slope from walls 30 to form a frictional grip with the top surfaces of the needle holder bases 20.

Referring now to FIGS. 4 and 5, a further embodiment 40 of organizer dispenser device of the invention is shown. In this arrangement, each of the individual needle holders 12 are positioned in a somewhat cantilever fashion from the upright support structure 46 of device 40. As can be seen in FIG. 5, a plurality of needle holders 12 may be positioned on either side of base 46 in cantilever fashion with individual holders 12 "hanging" in opposed relation to each other as shown in FIG. 5. In this arrangement, again, the holders may be twisted 90° so that the shorter diametrically opposed straight surfaces 26 may be positioned, as base 20 is shown on the right-hand end of FIG. 4, for passing through the opposed surfaces 60, 62 of the opposed wall portions 50, 52 of device 40.

The base 46 has a well like arrangement 56, as shown in FIG. 5 for retaining the larger rounded dimension surfaces 24 of each of the holder bases 20 until such time as the individual holders are dispensed. As can be seen in FIG. 4, organizer device 40 includes opposed end walls 42, 44 for maintaining the stability of the device 40. Device 40 may, for example, hold 20 needle holders. However, it will be understood that it is within the purview of this invention to have either organizer dispenser device 10 or 40 longer or shorter for containing a greater or smaller quantity of holders, depending upon user requirements.

As a further feature of this invention, the basic u-shaped structure of the needle holder organizer feature of the device of the invention may be modified, as discussed previously, in order to take advantage of a resilient and/or spring action which has the effect of holding, in flexible frictional engagement, the individual needle holders prior to such time as they are withdrawn for use from the device of the invention. Thus, in the embodiment 70 shown in FIG. 6, a needle holder 71 is shown in partial elevation with a base 82. As will be understood by practitioners-in-the-art, the curved opposed edges of the larger dimension of the base such as 82 in FIG. 6 includes as a generally routine construction an upright protuberance 84 which is integral with base 82. In this case, needle holder 71 is one comprised of a base 82 of relatively thin flexible material.

Thus, the dispenser organizer device 70 shown in FIG. 6 has uprights 74, 76 with opposed horizontal flanges 80, 78, respectively. However, the base 72 of device 70 has been modified so that the upper surface 73 thereof is inclined from each of the uprights 74, 76 to a point 75 centrally of the base surface 73. Because of this, the individual bases 82 of needle holders 71 are flexed when they are wedged into place in the position shown in FIG. 6. Because of this, further, the top surface 86 of each of the protuberances 84 are frictionally wedged under the surfaces 88 of the horizontal opposed flanges 78, 80. For this reason, each of the individual holders 71 remain in place once they are positioned in the device 70, until such time as they are to be used and removed from the device 70, as desired. Such an arrangement may be used alone or in combination with the protuberances 22 discussed previously.

Figure 7:
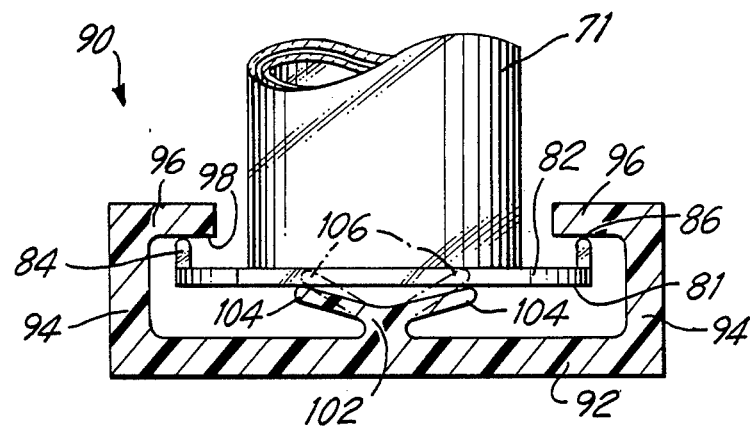
FIG. 7 is a sectional view of a further embodiment of organizer arrangement for retaining the individual needle holders in place in the dispenser organizer device of the invention.

FIG. 7 shows an additional embodiment of dispenser organizer device having imparted thereto a resilient spring action arrangement for engaging base 82, again in the relatively thin flexible form, of a needle holder 71 inserted therein. In this arrangement, the dispenser device is designated generally 90 with a base structure 92 having opposed upright walls 94 and opposed horizontal flanges 96 extending therefrom. As will be understood, all of these parts are preferably molded as an integral piece including the central spring like structure 102 shown in FIG. 7. Structure 102 extends from base 92 and includes diametrically opposed flexible spring-like wings 104 shown in solid lines in position for retaining the base 82 of holder 71. The wings 104 are shown in phantom at 106 when the needle holder device and its related base 82 are removed. The top surfaces 86 of the protuberances 84 engage the surface 98 of the opposed horizontal flanges 96 for engaging the opposite side of base 82 in frictional engagement with the flexible wings 104.

Figure 8:
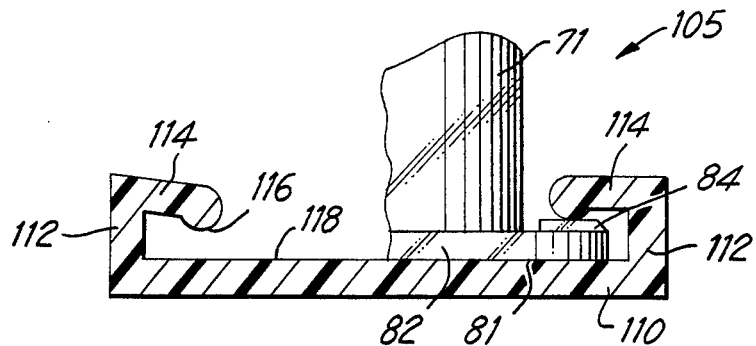
FIG. 8 is a sectional view of a still further embodiment showing a resilient organizer arrangement for holding the individual needle holders in place in the dispenser organizer device of the invention, with the left half of FIG. 8 showing one position of the organizer device prior to insertion of a holder and the right half showing the positioning of the device once a holder has been inserted.

FIG. 8 shows a still further arrangement for frictionally engaging a base 82 of a needle holder 71. In this arrangement, the dispenser organizer device of the invention is generally designated 105 having an elongated base 110 with upright opposed walls 112 and integral horizontal flanges 114 extending in diametrically opposed relation to each other. The left-hand side of FIG. 8 shows the position of the horizontal flange 114 prior to insertion of a holder 71 against the top surface 118 of base 110. The right-hand portion of FIG. 8 shows the positioning of the horizontal flange 114 once the base 82 of holder 71 is twisted into place. In this case, the integral protuberance 84 has the effect of forcing up the horizontal flange 114 in a "sprung-open" position.

Thus, a wedging action takes place between the top surface 118 of base 110 and the bottom surface 81 of the needle holder base 82 on one side of the needle holder base 82, while the wedging action between protuberance 84 and the diametrically opposed horizontal flanges 114 takes place between the top surface of the protuberances 84 and the bottom surface 116 of the horizontal diametrically opposed flanges 114.

As will be appreciated from the above, there is provided in accordance with this invention, a needle holder organizer and dispenser device which holds a plurality of needle holders in neat retained fashion until they are required for use. The device has the effect of providing order in a nursing station, and reducing the surface area required for maintaining a plurality of needle holders in place for use sequentially during a working day. Nevertheless, the device of the invention retains the holders in proper position by frictional engagement or otherwise until such time a they are to be used. The holders may be readily removed by simple rotation 90° when one is required for use.

While the forms of apparatus herein describe constitute preferred embodiments of the invention, it is to be understood that the invention is not limited to these precise forms of apparatus, and that changes may be made therein without departing from the scope of the invention which is defined in the appended claims. For example, whereas the forms of spring arrangement shown and described may develop their resiliency and spring action from the flexibility of the thermoplastic material of which the devices are formed, it will be understood that the configurations of spring structures may be comprised of metal as a separate portion of the dispenser device of the invention in order to provide the appropriate spring action, as required. Moreover, a plurality of devices such as 10 shown in FIG. 1 may be joined together side by side in order to provide a much larger dispensing arrangement for holding, for example thirty holders 12 in three devices 10 joined together side by side. Also, the dispenser device of the invention may include a conventional spring biased clip for clipping the organizer of the invention to the side edge of a nursing tray, for example, to reduce space reguirements within the tray.

What is claimed is:

1. An assembly for organizing a plurality of blood sample needle holders in orderly fashion prior to use at a nursing tray or cart, characterized by
    (a) an elongated substantially flat base;
    (b) said elongated substantially flat base having a top surface and a bottom surface;
    (c) an integral wall extending at right angles from each side edge of said flat base;
    (d) each said integral wall extending in the same direction from said base to form a generally u-shaped structure;
    (e) an integral flange extending at right angles from the edge of each of said walls opposite said base;
    (f) each said flange extending toward each other to a point spaced from each other to define a holder receiving space; and
    (g) each said flange being substantially parallel to said base to define a blood sample needle holder base receiving space;
    (h) a plurality of blood sample needle holders;
    (i) each said blood sample needle holder including
        (1) a tubular body having a substantially closed one end and an open end;
        (2) said substantially closed end having an opening positioned centrally thereof;
        (3) said centrally positioned opening having screw threads therein for receiving a double-ended needle for taking a blood sample;
        (4) an integral base flange extending outwardly from said open end;
        (5) two diametrically opposed side edges on said base flange being straight;
        (6) two diametrically opposed side edges on said base flange being curved; and
        (7) the distance between said curved side edges being greater than the distance between said straight edges.

2. The assembly of claim 1, further characterized by
(a) each of said curved edges includes an integral protuberance extending substantially at right angles to said base flange toward said closed end of said blood sample needle holder.

3. The assembly of claim 1, further characterized by
(a) said top surface of said base being inclined upwardly from each of said integral walls;
(b) said inclined top surface forming a raised point along the centerline of said inclined top surface; and
(c) whereby the base flanges of said blood sample needle holders are wedged between the bottom surfaces of said integral flanges and said inclined top surface.

4. The assembly of claim 1, further characterized by
(a) an elongated integral upright positioned along the center line of the top surface of said flat base;
(b) a flexible integral wing extending outwardly on each side of said integral upright;
(c) each said flexible wing extending cantilever from the end of said upright opposite said base to a point spaced from one of said integral walls;
(d) whereby the base flanges of said blood sample needle holders are wedged between the bottom surfaces of said integral flanges and the top surfaces of said flexible wings.

5. The assembly of claim 1, further characterized by
(a) an integral extension extending downwardly from the bottom surface of each said flange toward the top surface of said elongated base;
(b) said integral extension being positioned on each said integral flange at the end thereof opposite its respective integral wall; and
(c) whereby the base flanges of said blood sample needle holders are wedged between said integral extensions and said top surface of said elongated base.

6. The assembly of claim 1, further characterized by
(a) a plurality of integral protuberances extending from said top surface of said elongated base; and
(b) said plurality of protuberances being spaced apart for engaging the side edges of the base flanges of said blood sample needle holders positioned therein.

7. The assembly of claim 1, further characterized by
(a) a plurality of protuberances extending from the bottom surfaces of each of said flanges; and
(b) said plurality of protuberances extending into said blood sample needle holder space and being spaced apart for engaging the side edges of the base flanges of said blood sample needle holders positioned therein.

* * * * *